United States Patent
Syrinek

(10) Patent No.: US 7,682,491 B2
(45) Date of Patent: Mar. 23, 2010

(54) ANTIFOULANT FOR HYDROCARBON PROCESSING EQUIPMENT

(75) Inventor: Allen R. Syrinek, Richmond, TX (US)

(73) Assignee: Nalco Company, Naperville, IL (US)

( * ) Notice: Subject to any disclaimer, the term of this patent is extended or adjusted under 35 U.S.C. 154(b) by 319 days.

(21) Appl. No.: 11/691,209

(22) Filed: Mar. 26, 2007

(65) Prior Publication Data

US 2008/0241095 A1    Oct. 2, 2008

(51) Int. Cl.
    *A61K 31/74*    (2006.01)
(52) U.S. Cl. ............... 203/7; 208/48 AA; 208/48 R; 424/78.09
(58) Field of Classification Search ............... 208/48 R, 208/255; 203/7; 424/78.09
See application file for complete search history.

(56) References Cited

U.S. PATENT DOCUMENTS

| | | | |
|---|---|---|---|
| 3,087,436 A | 4/1963 | Dettlof et al. | |
| 3,231,587 A | 1/1966 | Rense | |
| 3,245,707 A | 4/1966 | Cook | |
| 3,271,295 A | 9/1966 | Gonzalez | |
| 3,271,296 A | 9/1966 | Gonzalez | |
| 3,272,746 A | 9/1966 | Le Suer et al. | |
| 3,361,673 A | 1/1968 | Stuart et al. | |
| 3,437,583 A | 4/1969 | Gonzalez | |
| 3,712,892 A | 1/1973 | Inaba et al. | |
| 3,912,764 A | 10/1975 | Palmer, Jr. | |
| 4,110,349 A | 8/1978 | Cohen | |
| 4,234,435 A | 11/1980 | Meinhardt et al. | |
| 4,883,886 A * | 11/1989 | Huang ..................... 549/255 |
| 5,110,997 A | 5/1992 | Dickakian | |
| 5,194,620 A | 3/1993 | Roling et al. | |
| 5,240,469 A | 8/1993 | Poindexter | |
| 5,433,757 A * | 7/1995 | Song et al. ................ 44/393 |
| 5,435,926 A * | 7/1995 | Gutierrez et al. ........... 508/507 |
| 2003/0163947 A1 * | 9/2003 | Rivolta et al. .............. 44/301 |

OTHER PUBLICATIONS

"Antifoulant for ethylene dichloride processing"; Research Disclosure, 356; 793; No. 35628; Coden: RSDSBB; ISSN: 0374-4353; 1993, Abstract Only.

* cited by examiner

*Primary Examiner*—Glenn A Caldarola
*Assistant Examiner*—Brian McCaig
(74) *Attorney, Agent, or Firm*—Benjamin E. Carlsen; Michael B. Martin

(57) ABSTRACT

A method of using substituted olefin polymers prepared by reacting one or more $C_2$-$C_{10}$ mono-olefin polymers having a number average molecular weight of about 300 to about 5,000 with $C_4$-$C_{10}$ monounsaturated dicarboxylic acid derivatives and compositions comprising the substituted olefin polymers for preventing fouling of hydrocarbon processing equipment, especially ethylene dichloride distillation units.

19 Claims, No Drawings

ANTIFOULANT FOR HYDROCARBON PROCESSING EQUIPMENT

TECHNICAL FIELD

This invention relates to certain olefin polymers substituted with monounsaturated dicarboxylic acid derivatives, formulations comprising the polymers, and their use for preventing fouling of hydrocarbon processing equipment, particularly ethylene dichloride distillation units.

BACKGROUND OF THE INVENTION

In the processing of petroleum hydrocarbons and feedstocks such as petroleum intermediates, and petrochemicals and petrochemical intermediates, e.g., gas, oils and reformer stocks, chlorinated hydrocarbons and olefin plant fluids the hydrocarbons are commonly heated to temperatures of 50° C. to 600° C. Exposure of the hydrocarbon liquids to these elevated temperatures can result in the formation of fouling deposits on the hydrocarbon processing equipment. In many processes, the deposits reduce the bore of conduits and vessels and impede process throughput, impair thermal transfer, and clog filter screens, valves and traps. In the case of heat exchange systems, the deposits form an insulating layer upon the available surfaces to restrict heat transfer and necessitate frequent shut-downs for cleaning. Moreover these deposits reduce throughput, which of course, results in a loss of capacity with a drastic effect in the yield of finish product. Accordingly, these deposits have caused considerable concern to the industry.

For example, in the production of vinyl chloride monomer (VCM), either ethylene, oxygen and HCl are reacted in an oxychlorination unit or ethylene and chlorine are reacted in a direct chlorination unit to produce ethylene dichloride (EDC) that is then processed in a cracking unit to form the VCM. The plant normally includes recycling facilities to recover residual EDC from the cracking unit and purification facilities used to purify EDC from recycle, oxychlorination and direct chlorination.

Serious fouling occurs in the various units handling the liquid EDC. For example, in the primary EDC recovery unit, fouling occurs in the distillation trays and the transfer facilities, especially the reboilers. Fouling is particularly serious in the liquid phase of EDC in the primary EDC recovery unit, heavies column and the vacuum column. It is not uncommon for the fouling to require plant shutdown after only a few months of operation.

The fouling is believed to be due to highly chlorinated and/or oxygenated polymeric materials which are incompatible in the EDC stream.

A method prevent fouling of equipment used in the manufacture of ethylene dichloride using acylated amines prepared by reacting a $C_2$-$C_{10}$ mono-olefin polymer substituted with a $C_4$-$C_{10}$ monounsaturated dicarboxylic acid derivative and a basic amine; oil-soluble magnesium alkyl aromatic sulfonate; and combinations thereof is disclosed in U.S. Pat. No. 5,110,997.

SUMMARY OF THE INVENTION

In an embodiment, this invention is a method of preventing fouling of hydrocarbon processing equipment in contact with hydrocarbon fluids during processing of said hydrocarbon fluids comprising adding to said fluids an effective antifouling amount of one or more substituted olefin polymers prepared by reacting one or more $C_2$-$C_{10}$ olefin polymers having a number average molecular weight of about 150 to about 5,000 with one or more $C_4$-$C_{10}$ monounsaturated dicarboxylic acid derivatives.

In an embodiment, this invention is a composition comprising one or more organic solvents and about 5 to about 80 weight percent of one or more substituted olefin polymers prepared by reacting one or more $C_2$-$C_{10}$ mono-olefin polymers having a number average molecular weight of about 150 to about 5,000 with one or more $C_4$-$C_{10}$ monounsaturated dicarboxylic acid derivatives.

DETAILED DESCRIPTION OF THE INVENTION

The antifoulant of this invention is substituted olefin polymer or "OPDA" prepared by reacting one or more long chain $C_2$-$C_{10}$ olefin polymers having a number average molecular weight of about 150 to about 5,000 with one or more $C_4$-$C_{10}$ monounsaturated dicarboxylic acid derivatives. Representative dicarboxylic acid derivatives include fumaric acid, itaconic acid, maleic acid, maleic anhydride, chloromaleic acid, dimethyl fumarate, chloromaleic anhydride, and the like.

Representative $C_2$-$C_{10}$ olefins include ethylene, propylene, butylene, isobutylene, pentene, octene-1, styrene, and the like. The olefin polymers can be homopolymers such as polyisobutylene, as well as copolymers of two or more of such olefins such as copolymers of ethylene with isobutylene; etc. Other copolymers include those in which a minor molar amount of the copolymer monomers, e.g., 1 to 10 mole percent is a $C_4$ to $C_{18}$ conjugated diolefin, e.g., a copolymer of isobutylene and butadiene; or a copolymer of ethylene, propylene, and 1,4-hexadiene; etc.

In an embodiment, the olefin polymer comprises $C_2$-$C_5$ olefins. In an embodiment, the olefin polymer has an about one terminal double bond per polymer chain. In an embodiment, the olefin polymer is polyisobutylene.

In an embodiment, the long chain hydrocarbon is substituted with at least one molar equivalent of $C_2$-$C_{10}$ monounsaturated dicarboxylic acid derivatives.

In an embodiment, the substituted olefin polymer is polyisobutylene substituted with succinic anhydride groups.

In an embodiment, the olefin polymers have a number average molecular weight of about 200 to about 3,000. In another embodiment, the olefin polymers have a number average molecular weight of about 500 to about 1,200. The number average molecular weight for such polymers can be determined by several known techniques.

The reaction of the olefin polymer with the dicarboxylic acid derivative to form the substituted olefin polymer is typically carried out at elevated temperature in the presence of chlorine. Processes for reacting the olefin polymer with the unsaturated dicarboxylic acid derivative are known in the art and are described, for example, in U.S. Pat. Nos. 3,361,673; 3,087,436; 3,712,892; 3,272,746; 3,245,707; 3,231,587; 3,912,764; 4,110,349; and 4,234,435. Suitable substituted olefin polymers are also commercially available, for example from Chevron Oronite, Houston, Tex. under the tradename OLOA.

The OPDA's limit fouling of equipment used in the synthesis, purification and use of hydrocarbons, particularly hydrocarbon streams that can form insoluble components. OPDAs particularly limit fouling in chlorinated solvents like methylene chloride, chloroform, and most specifically EDC which is used to manufacture vinyl chloride monomer. OPDAs are also useful as antifoulants in the synthesis, purification and use of vinyl chloride and other vinyl containing chlorinated monomers, such as chloroprene, vinylidene, trichloroethylene, and the like where acylated amines as reported in U.S. Pat. No. 5,110,977 have proven useful. Similarly OPDAs limit fouling in the production, purification, and polymerization of other vinyl monomers including acrylic acid, vinyl acetate, styrene, butadiene, and the like where compounds similar to the acylated amine reported in U.S. Pat. No. 5,110,977 and the polymethacrylate ester reported in U.S. Pat. No. 5,240,469 have found use.

In an embodiment, the hydrocarbon processing equipment is selected from the group consisting of ethylene dichloride distillation units.

In an embodiment, the OPDA is formulated in an organic solvent for introduction into the hydrocarbon fluids. Suitable organic solvents include, but are not limited to aliphatic hydrocarbons such as diesel and kerosene, naphthenic solvents including heavy aromatic naphtha "HAN", chlorinated solvents such as methylene chloride and aromatic solvents such as toluene. In an embodiment, the solvent is kerosene.

In an embodiment, the formulation comprises about 5 to about 80 weight percent of OPDA in the organic solvent.

In a typical application, the formulation comprising OPDA and organic solvent is introduced into the EDC production system to protect equipment exposed to crude EDC at temperatures between about 75 and about 300° C. The formulation may include other additives known in the art including antioxidants, anti-polymerants, metal deactivators, and the like.

The amount of OPDA added to the system may be empirically determined based on the characteristics of the particular system being treated. In an embodiment, the concentration of OPDA may range from about 10 to about 500 ppm. In another embodiment, the concentration of the substituted olefin polymer may range from about 25 to about 300 ppm based on the weight of the EDC feed stream.

The locations of OPDA introduction can include the crude ethylene dichloride feed to the EDC recovery tower which is generally operated at 75 to 200° C. and can also include the feed to the EDC vacuum column or tar still, operated at 100 to 300° C. The term "crude ethylene dichloride" refers to unpurified EDC which leaves the chlorination or oxychlorination units. Crude EDC also refers to the feed streams for the recovery, heavies and vacuum columns. These units may be considered distillation separation units that separate the crude EDC stream into an overhead stream of purified EDC and a bottoms stream of EDC, 1,1,2-trichloroethane, hexachloroethane, hexachlorobenzene, with fouling amounts of chlorinated or oxychlorinated polymeric material or inorganic materials such as iron and sodium salts. The fouling in the bottoms is severe at EDC levels below about 30 weight percent, and particularly severe at EDC levels of 20 weight percent or below. At high EDC levels in the bottoms, EDC acts as a solvent for the fouling materials. The present invention thus permits the EDC unit to operate efficiently at high EDC recovery with corresponding low EDC levels in the bottoms. The OPDA functions as a dispersant for the fouling materials in the bottoms thereby inhibiting fouling therein. The present invention enables the EDC unit to operate at relatively long periods of time at decreased EDC levels in the bottoms.

The foregoing may be better understood by reference to the following examples, which are presented for purposes of illustration and are not intended to limit the scope of the invention.

EXAMPLE

A Hot Liquid Process Simulator (HLPS) is used to simulate heat exchanger fouling in EDC purification. In the HLPS, a liquid stream is circulated into a heat exchanger housing a carbon steel heater tube. The heater tube can be heated from 50-600° C. metal temperature. A high fouling liquid stream will form deposits on the heater surface which necessitates increased heating tube temperature to maintain a set liquid outlet temperature. An increase in the heating tube temperature is a measure of fouling (i.e. the temperature difference between the heating tube and outlet increases). The fouling rate can be determined by plotting the change in heating rod temperature versus time. The slope of the resulting line is the fouling rate. These fouling rates are used to calculate percent inhibition for antifoulants by comparison to the fouling rate of a particular stream with no antifoulants. Calculating the percent inhibition allows direct comparison of performances of different antifoulants.

A representative antifoulant according to the invention used in the tests is polyisobutylene having a molecular weight of about 1,000 substituted with succinic anhydride ("PIBSA"), available from Chevron Oronite, Houston, Tex., as OLOA 15500. For the experiments described herein, the PIBSA is formulated as a 60 weight percent solution in kerosene. Commercial 1 is a blend of polyisobutylene/polyamine and over-based magnesium sulfonate according to U.S. Pat. No. 5,110,997, available from Nalco Company, Naperville, Ill. Comparison testing of PIBSA and Commercial 1 is performed on the streams described below. The results are summarized in Table 1.

Stream 1: Vacuum bottoms sample containing 2.6% tars, 180-ppm Fe, 23-ppm Na, and 3.7% EDC. The low EDC concentration and high sodium are the major contributors to fouling. Because of the low EDC concentration, dispersants do not work well even at a low outlet temperature of 149° C.

Stream 2: Vacuum bottoms sample similar to Stream 1 except containing more residual EDC, 15.3%. The fouling rate is lower and the tests are run at a higher temperature, 170° C., in order to obtain a substantial fouling rate.

Stream 3: Heavy bottoms sample that was not analyzed.

Stream 4: Heavy bottoms sample, not analyzed, that did not show substantial fouling until the outlet temperature of the test was set at 190° C.

Stream 5: Synthetic stream prepared by blending 100-ppm ferric ions from iron acetylacetonate and 2400-ppm polychloroprene (50 Mooney Viscosity) in chromatography grade EDC from Aldrich. When the solution is allowed to set over night a substantial fouling rate is achieved.

TABLE 1

| Stream | Additive | Dose (ppm) | % Inhibition |
|---|---|---|---|
| 1 | PIBSA solution | 50 | 30 |
|   | Commercial 1 | 200 | 37 |
| 2 | PIBSA solution | 35 | 100 |
|   | Commercial 1 | 200 | 84 |
| 3 | PIBSA solution | 50 | 77 |
|   | Commercial 1 | 50 | 90 |
| 4 | PIBSA solution | 400 | 99 |
|   | Commercial 1 | 400 | 97 |
| 5 | PIBSA solution | 108 | 100 |
|   | Commercial 1 | 100 | 98 |

These data indicate that a representative composition according to the invention inhibits fouling at much lower dosage than a current commercial treatment in vacuum bottom samples. It also shows that performance is similar at similar dosages of the commercial treatment for heavy bottoms samples and a synthetic stream containing ferric ions and polychloroprene. In all cases, fouling inhibition equivalent to the commercial treatment (often at lower dosage) is obtained with the composition of the invention. Since this material costs less, it is a superior antifoulant to the existing commercial treatment.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of preventing fouling of hydrocarbon processing equipment in contact with hydrocarbon fluids containing between 3.7% and 15.3% ethylene dichloride during processing of said hydrocarbon fluids comprising adding to said fluids an effective antifouling amount of one or more substituted olefin polymers prepared by reacting one or more $C_2$-$C_{10}$ olefin polymers having a number average molecular weight of about 150 to about 5,000 with one or more $C_4$-$C_{10}$ monounsaturated dicarboxylic acid derivatives.

2. The method of claim 1 wherein said hydrocarbon processing equipment is selected from the group consisting of ethylene dichloride distillation units.

3. The method of claim 2 wherein the substituted olefin polymers are added to the feed to the distillation units.

4. The method of claim 3 wherein said olefin polymer is reacted with at least one molar equivalent of said monounsaturated dicarboxylic acid derivatives.

5. The method of claim 4 wherein said olefin polymer comprises $C_2$-$C_5$ mono-olefins.

6. The method of claim 5 wherein said olefin polymer is polyisobutylene.

7. The method of claim 6 wherein said olefin polymer has a number average molecular weight of about 200 to about 3,000.

8. The method of claim 7 wherein said substituted olefin polymer is polyisobutylene substituted with succinic anhydride groups.

9. The method of claim 7 wherein said olefin polymer has a number average molecular weight of about 500 to about 1,200.

10. The method of claim 1 wherein said substituted olefin polymer is formulated in one or more organic solvents.

11. The method of claim 10 wherein said solvent is kerosene.

12. A composition comprising one or more organic solvents and about 5 to about 80 weight percent of one or more substituted olefin polymers prepared by reacting one or more $C_2$-$C_{10}$ mono-olefin polymers having a number average molecular weight of about 150 to about 5,000 with one or more $C_4$-$C_{10}$ monounsaturated dicarboxylic acid derivatives.

13. The composition of claim 12 wherein said olefin polymer is reacted with at least one molar equivalent of said monounsaturated dicarboxylic acid derivatives.

14. The composition of claim 13 wherein the olefin polymer comprises $C_2$-$C_5$ mono-olefins.

15. The composition of claim 14 wherein said olefin polymer is polyisobutylene.

16. The composition of claim 15 wherein said olefin polymer has a number average molecular weight of about 200 to about 3,000.

17. The composition of claim 16 wherein said substituted olefin polymer is polyisobutylene substituted with succinic anhydride groups.

18. The composition of claim 17 wherein said olefin polymer has a number average molecular weight of about 500 to about 1,200.

19. The composition of claim 18 wherein said organic solvent is kerosene.

* * * * *